(12) United States Patent
Westermann et al.

(10) Patent No.: US 7,358,382 B2
(45) Date of Patent: Apr. 15, 2008

(54) PROTECTED 3,5-DIHYDROXY-2,2-DIMETHYL-VALERONITRILES FOR THE SYNTHESIS OF EPOTHILONES AND EPOTHILONE DERIVATIVES AND PROCESS FOR THE PRODUCTION

(75) Inventors: Jurgen Westermann, Berlin (DE); Johannes Platzek, Berlin (DE); Orlin Petrov, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 315 days.

(21) Appl. No.: 11/188,991

(22) Filed: Jul. 26, 2005

(65) Prior Publication Data

US 2005/0267306 A1 Dec. 1, 2005

Related U.S. Application Data

(62) Division of application No. 10/211,236, filed on Aug. 5, 2002, now Pat. No. 7,034,165.

(60) Provisional application No. 60/313,016, filed on Aug. 20, 2001.

(30) Foreign Application Priority Data

Aug. 3, 2001 (DE) ................ 101 38 347

(51) Int. Cl.
C07C 255/03 (2006.01)

(52) U.S. Cl. ............... 558/398; 558/435; 558/441

(58) Field of Classification Search ............... 558/398, 558/435, 441

See application file for complete search history.

(56) References Cited

U.S. PATENT DOCUMENTS 6,730,803 B2 5/2004 Iwasaki et al.

FOREIGN PATENT DOCUMENTS

WO WO 00/58254 10/2000

OTHER PUBLICATIONS

Statutory Disclaimer of claims 1, 2, 9, 10, 25 and 26 in U.S. 6,730,803 by patent owner.
Schinzer D et al: Chemistry-A European Journal, vol. 2, No. 11, 1996, pp. 1477-1482.
Schinzer D et al: Angewandte Chemie, vol. 109, No. 5, 1997, pp. 523-524.
Johann Mulzer et al: J. Org. Chem., vol. 65, No. 22, 2000, pp. 7456-7467.
Alois Furstner, Christian mathes and Karol Grela Concise total synthesis of epothilone A and C based on alkyne metathesis *Max-Planck-Institut fur Kohlenforschung, Kaiser-Wilhelm-Platz 1, D-45470 Mulheim/Ruhr, Germany*. Received Feb. 20, 2001, Accepted May 8, 2001, First published as an Advance Article on the web May 25, 2001.

*Primary Examiner*—Rita Desai
*Assistant Examiner*—John Mabry
(74) *Attorney, Agent, or Firm*—Millen, White, Zelano, Branigan, P.C.

(57) ABSTRACT

The invention relates to 3,5-dihydroxy-2,2-dimethyl-valeronitriles for the synthesis of epothilones and epothilone derivatives and process for the production of these new intermediate products in the synthesis and the use for the production of epothilones or epothilone derivatives.

7 Claims, No Drawings

PROTECTED 3,5-DIHYDROXY-2,2-DIMETHYL-VALERONITRILES FOR THE SYNTHESIS OF EPOTHILONES AND EPOTHILONE DERIVATIVES AND PROCESS FOR THE PRODUCTION

This application is a divisional of U.S. Ser. No. 10/211,236, filed Aug. 5, 2002 now U.S. Pat. No. 7,034,165.

This application claims the benefit of the filing date of U.S. Provisional Application Ser. No. 60/313,016 filed Aug. 20, 2001.

The invention relates to the subject that is characterized in the claims, i.e., new intermediate products and process for their production and the use. The process for the production of new intermediate products starts from economical starting materials, yields the intermediate products in high enantiomer purities, in high chemical purity, in good yields and allows the industrial-scale production.

The invention is used in the synthesis of component A from natural and synthetically modified epothilones or derivatives. Epothilones are 16-membered macrolide rings that were isolated from the cultures of Myxobacterium Sorangium Cellosum and are representatives of a class of promising anti-tumor agents that were tested and found to be effective against a number of cancer lines. A survey of the syntheses has been described by J. Mulzer et al. in J. Org. Chem. 2000, 65, 7456-7467.

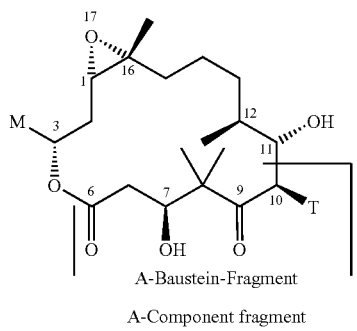

A-Component fragment

In the literature, in addition to the natural epothilones, a number of synthetic epothilone derivatives are described that vary for the most part within radicals M and T. In most cases, M stands for a heterocyclic radical here. Most syntheses of the natural epothilones and the synthetic epothilone derivatives use the A-component fragment, which represent carbon atoms $C_5$-$C_{10}$ in the macrolide. Within this component A (see below), $C_1$ is the $C_5$ in the macrolide and $C_6$ is the $C_{10}$ in the macrolide, etc.

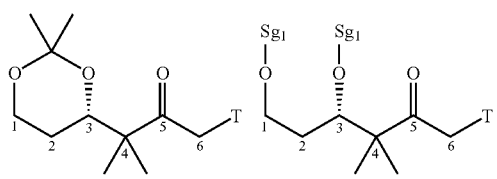

In this connection, T stands for a C1-C4 alkyl or alkenyl radical, and Sg1 and Sg2 stand for the protective groups that are familiar to one skilled in the art, such as, e.g., the TBDMS group.

A possible production of the A-component is described in, for example, WO00/58254. A synthesis of β-keto esters, which can be converted in multistage sequences into component A, is disclosed therein. The chirality is introduced by an asymmetric hydrogenation of a β-keto ester according to Noyori:

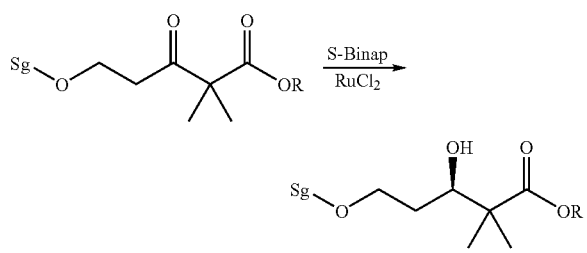

In this connection, the conversion of the ester group into a ketone can only be done by means of a multistage sequence. In this case, after a protection of the 1- and 3-hydroxy group, the ester group (C-5 atom) is reduced to form alcohol, the oxidation to aldehyde is carried out, the Grignard addition of an alkyl radical with an alkylmagnesium or alkyllithium compound yields a secondary alcohol, which then is oxidized. To get from the ester to the ketone, a total of 8 steps are necessary. The direct reaction of an ester is not selective, since the intermediately produced product is further reacted. The following diagram shows the entire synthesis pathway:

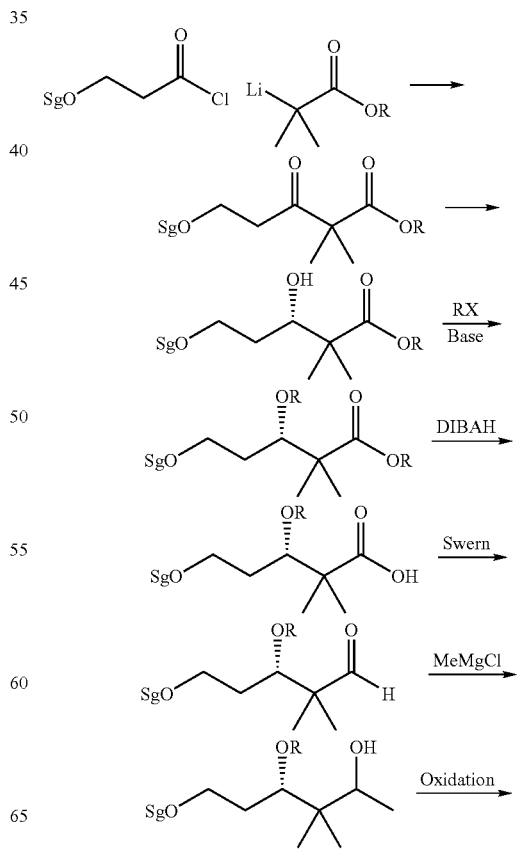

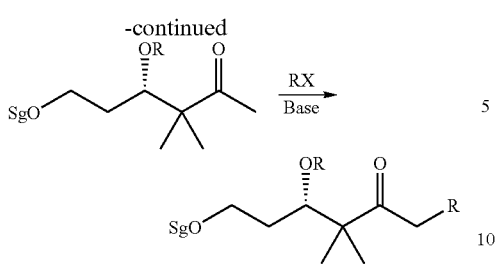

A method for creating component A is described by B. Paniker et al. in Tetrahedron 2000, 56, 78-59-7868. It is described there that the aldol reaction with a chiral component yields a less selective reaction. By the round-about way of an N-methylthioacetyl-oxazolidinone, the synthesis of the chiral C3 atom in a multistage sequence with improved diastereoselectivity by means of boron enolate is described. To achieve usable diastereoselectivities, a methylthio substitution is necessary; the thio ether is cleaved off after the aldol reaction.

Further, a sequence can be found in the prior art (R. E. Taylor, Y. Chen, Org. Lett. (2001), 3(14), 2221-2224) in which a phenyl ester is used for the Grignard reaction. The yield that is achieved in this case is indicated with 77%. In the example that is described by A. Fürstner in Chem. Comm. 2001, 1057-1059, a 67% yield is achieved. These yields of the Grignard reaction from the prior art are significantly less than those of this invention.

In J. Org. Chem. 2000, 65, 7456-7467, an asymmetrical synthesis of a β-keto ester is further described, whereby a variant in asymmetrical form is performed as an aldol reaction. In this method, D-Ts-valine is used as a catalyst, which can be produced from the expensive amino acid D-valine. This method yields an ee-value of 90%. Another example in this regard is described by R. E. Taylor, Y. Chen, Org. Lett. (2001), 3(14), 2221-2224 as an asymmetrical aldol reaction, in which the yield is 71%.

Another method for the production of a double TBDMS-protected A-component-ethyl ketone is finally described by Nicolaou in Chem. Eur. J. 2000, 6, 2783-2800.

This invention contains the object of being able to produce a universally usable starting intermediate compound of general formula I as well as the optically pure antipodes of general formulas Ia, Ib,

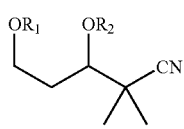

(I)

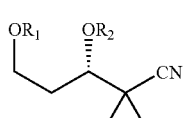

(Ia)

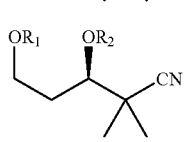

(Ib)

in which R1, R2 can be the same or different and, independently of one another, stand for an alcohol protective group that is familiar to one skilled in the art, for example, benzyl, 4-methoxybenzyl, 3,4-dimethoxybenzyl, THP, TBDMS, TMS, TES, TIP, TBDPS, MEM, MOM, allyl, trityl, or, in the case when R1 and R2 are bridged, stand for a ketal protective group, such as, e.g.,

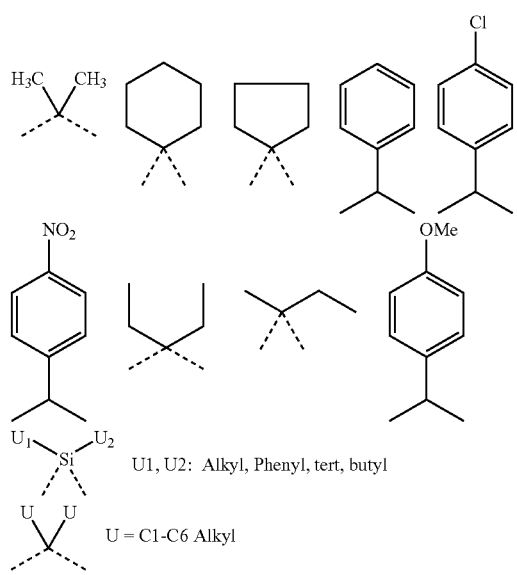

to produce A-component fragments for epothilone total syntheses.

To this end, compounds of general formula I are reacted as described below:

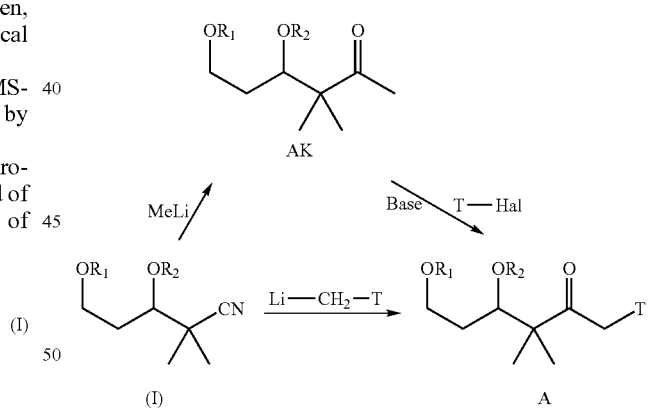

The reactions of the compounds of general formula I, as well as their antipodes Ia, Ib to form ketones AK are carried out with methyllithium or methyl-Grignard compounds according to the standard process that is known to one skilled in the art; the aqueous working-up then yields the ketone. The subsequent alkylation with an alkyl or alkenyl-halide of formula T-Hal (Hal=Cl, Br, I or tosylate, mesylate, triflate, etc.) with the addition of a base yields the A-component fragments.

A can also be directly obtained, however, by the amides of general formula I being reacted directly with organometallic compounds, such as, e.g., the lithium compound Li—CH2-T and then being worked up in aqueous form.

As a rule, the above-described reactions run smoothly and produce the A components in high yields.

There was therefore a need for an industrial-scale process that allows it to prepare a universally usable intermediate compound for the production of the A component in the epothilone total synthesis.

In addition to the high yields in the conversion into the A components, the relatively easy accessibility of the compounds of general formula I from relatively inexpensive starting materials can be emphasized. Moreover, the compounds according to the invention are stable in storage in contrast to the esters and ketones that are known in the literature and can be reacted as needed during a continuous synthesis campaign. For the most part, the compounds of general formula I are crystalline solids and can be purified by crystallization. In this way, high chemical and optical yields (e.e. >98%) can be achieved.

The object of the invention is achieved by the preparation of the new compounds of general formulas I, Ia, Ib

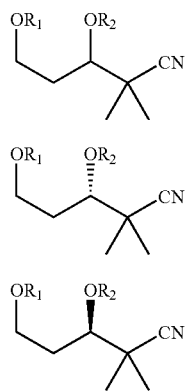

in which R1, R2 can be the same or different, and, independently of one another, stand for an alcohol protective group, such as, e.g., benzyl, 4-methoxybenzyl, 3,4-dimethoxybenzyl, THP, TBDMS, TMS, TES, TIP, TBDPS, MEM, MOM, allyl, trityl, or in the case when R1 and R2 are bridged, stand for a ketal protective group, such as, e.g.,

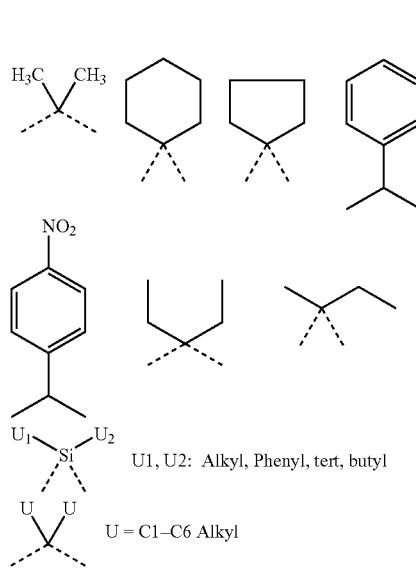

For the production of the compounds according to the invention, a total of 4 variants can be indicated:

Variant I (General Access Via Aldol Reactions)

a) In the case where R1 and R2 stand for a ketal protective group, or R1=R2, compounds of general formula I can be produced from compounds of formula II, 2,2-dimethyl-3,5-dihydroxy-valero-nitrile

according to the methods for protective group chemistry that are known to one skilled in the art; thus, for example, their production and cleavage are described in P. J. Kocienski in "Protecting Groups," Georg Thieme Verlag Stuttgart, New York, 1994, as well as in Houben Weyl, 4th Edition, Volume VI/1b, p. 737, Thieme Stuttgart 1984.

b) In the case that R1 and R2 do not represent any ketal-protective group but nevertheless can be the same or different, the production of the compounds of general formula I can be carried out directly from the compounds of general formula III, by protective group R2 being introduced according to methods that are known in the literature.

Compounds of general formula II can be produced from compounds of general formula III

in which R1 stands for a protective group in the above-indicated meaning, by cleavage of protective group R1 according to the process, known to one skilled in the art, of the protective group cleavage of alcohols (P. J. Kocienski in "Protecting Groups," Georg Thieme Verlag Stuttgart, New York 1994/Houben Weyl, 4th Edition Volume VI/1b p. 737, Thieme Stuttgart 1984).

Compounds of general formula III can be produced from compounds of general formula IV

by reaction with the compound of formula V, 2-methylpropionitrile,

in which R1 is in the above-indicated meaning, in a way that is known to one skilled in the art by the techniques of the aldol condensation.

The production of compounds of general formula IV are known to one skilled in the art, however:
R1=THP in JOC, 1984, 49, 2301-2309
R1=benzyl in J. Chem. Soc. Perk. Trans 1, 2000, 2429-2454,
R1=TBDMS in JOC, 2000, 65, 7456-7467

The compound of formula V, 2-methylpropionitrile, is a commercially available product.

Variant II (Production of Optically Active Intermediate Products of General Formula Ia)

For the production of optically active compounds of general formula Ia

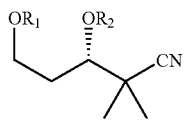
(Ia)

the procedure is analogous to that described under Variant I. Starting from the optically active intermediate stage of general formulas IIa and IIIa

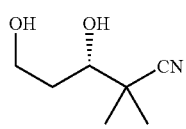
(IIa)

compounds of general formula Ia are produced.

Compounds of general formula IIa are produced analogously from the optically active precursors of general formula IIIa

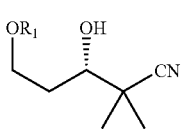
(IIIa)

Optically active compounds of general formula Ia are accessible as follows:

1. Separation of the racemic compound of general formula III in the chiral phase (Lit.: G. Roussel, P. Piras, Chirabase, Pure and Applied Chemistry, 1993, 65, 235-244), primarily by SMB technique: A. Seidel-Morgenstern et al., Chromat. A. 1998, 827/2, 175-191.
2. By starting from the racemic alcohol of general formula III, esters of general formula VI

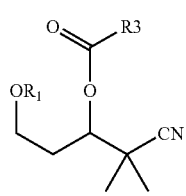
(VI)

in which R3 stands for a C1-C6 alkyl group or an allyl, phenyl or benzyl group, are produced according to the process of esterification that is known to one skilled in the art.

And the latter is saponified enantioselectively by enzymatic or microbiological methods. The alcohol that is produced is clearly distinguished in its Rf value from the ester that is used so that the two can easily be separated from another, e.g., by column chromatography.

3. By aldol condensation that is mediated with chiral catalysts, by compounds of general formulas IV and V being reacted with use of a catalytic or stoichiometric amount of a chiral aldol catalyst:

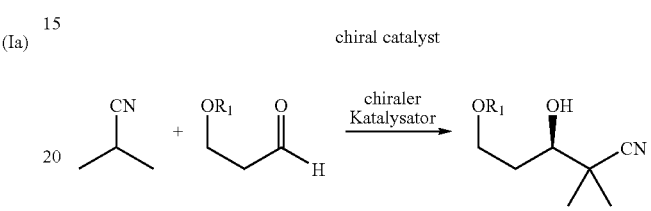

(V)     (IV)     (IIIa)

Literature: See, e.g., J. Org. Chem. 2000, 65, 7456-7467

4. By a chiral reduction of the ketone of general formula VII

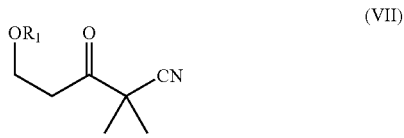
(VII)

being performed according to methods that are known to one skilled in the art. Lit.: Noyori et al., J. Am. Chem. Soc. 1987, 109, 5850; Noyori et al., J. Am. Chem. Soc. 1988, 110, 629, R. C. Larock in "Comprehensive Organic Transformations," VCH Publishers New York 1989, ISBN 0-89573-710-8, pages 540-548.

Compounds of general formula VII, with R1 in the above-indicated meaning, can be obtained by reaction of the compound of formula V with compounds of general formula VIII

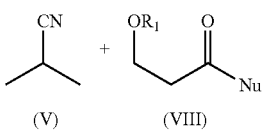
(V)     (VIII)

in which Nu stands for a leaving group, such as Cl, Br, imidazole, —OPh, —O—C6H4NO2, —O—C1-C4 alkyl, etc.

The reaction is carried out in a way that is known to one skilled in the art.

The production of compounds of general formula VIII is described in the literature: J. Med. Chem. 1999, 706-721.

In some cases, it has proven advantageous when compounds of general formula VII are produced by oxidation from the racemic alcohols of general formula II according to the methods of oxidation that are known to one skilled in the art (e.g., Swern oxidation, PDC, PCC, etc.).

In some cases, it has proven advantageous when a compound of formula V is reacted with propiolactone to form a compound of IX:

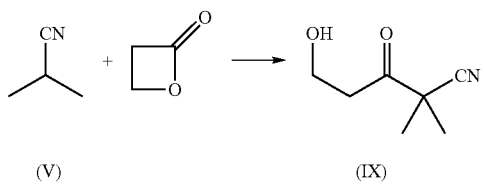

(V)    (IX)

The compound of formula IX can be converted very easily into compounds of general formula VII by introducing protective groups according to the methods that are known to one skilled in the art (see: P. J. Kocienski in "Protecting Groups," Georg Thieme Verlag Stuttgart, New York 1994, as well as in Houben Weyl, 4th Edition, Volume VI/1b, p. 737, Thieme Stuttgart 1984).

Starting from compounds of formula IX, however, a compound of formula IIa

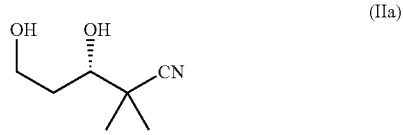

(IIa)

can be obtained by the keto group being reduced chirally with chemical or microbiological methods (e.g., according to: JOC1985, 50, 127/J. Chem. Soc., Chem. Commun. 1987, 1368).

Variant III

Compounds of general formula Ia

(Ia)

can also be produced by introducing protective groups according to methods that are known in the literature for introducing alcohol protective groups from the compounds of general formula X

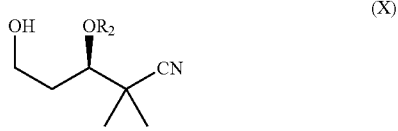

(X)

(see literature cited above for introducing protective groups).

Compounds of general formula X can be produced from compounds of general formula XI

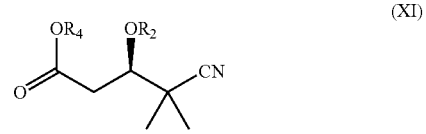

(XI)

in which R4 stands for a methyl, ethyl or benzyl group, by ester reduction according to methods that are known to one skilled in the art.

Compounds of general formula XI can be produced from compounds of general formula XII

(XII)

in which R4 stands for a C1-C6 alkyl, methyl, ethyl, tert-butyl, phenyl or benzyl group, by introducing protective group R2 according to methods that are known to one skilled in the art (see above).

Compounds of general formula XII can be obtained from β-keto esters of general formula XIII

(XIII)

by methods of chiral reduction (chemical or enzymatic).

Compounds of general formula XIII are obtained by reaction of compounds of general formula XIV with a compound of formula V

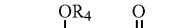

(XIV)

(V)

Compounds of general formula XIV are known in the literature or can be obtained from the reaction of compounds of general formulas XIIIa and XIIIb.

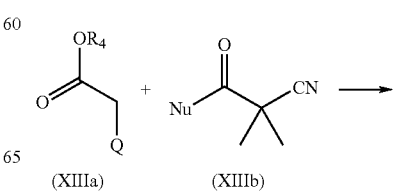

(XIIIa)    (XIIIb)

-continued

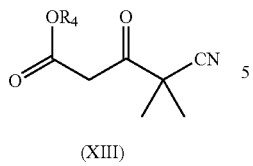

(XIII)

Here, Nu is in the meaning of the leaving group that is already mentioned above, and Q stands for a hydrogen atom or a COOH group. If Q is a hydrogen atom, XIIIa is deprotonated with an organic base, such as, e.g., LDA and then is reacted with the activated acid derivative according to the method that is familiar to one skilled in the art.

In the case of Q being equal to COOH, the procedure is performed with the methods of the malonic acid-semi-ester condensation, as described in, e.g., J. Am. Chem. Soc. 1999, 121, 7050-7062, Synth. Commun. 1997, 27, 3227-3234.

Compounds of general formula XIIIa are commercially available (e.g., Aldrich).

Compounds of general formula XIIIb are produced as described in R. C. Larock in "Comprehensive Organic Transformations," VCH Publishers New York 1989, ISBN 0-89573-710-8, pages 963-964.

In some cases, it has proven advantageous to run the diols of general formula IIa

(IIa)

directly through the compounds of general formula XII

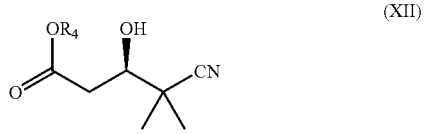

(XII)

by reduction of the ester group according to the above-mentioned process.

The production of racemic diol of general formula II can also use as starting compounds β-keto esters of general formula XIII

(XIII)

according to the commonly used methods for reduction of esters and ketones.

Variant IV

In some cases, for the production of optically active diols of general formula IIa, it has proven advantageous to undertake a chromatographic separation or crystallization of the diastereomeric ketals of general formulas XIVa and XIVb

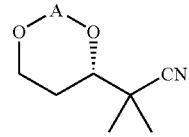

(XIVa)

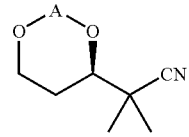

(XIVb)

in which A is taken for the radical of an optically active ketone, such as, e.g., (−) menthone, (−) camphor, etc., and then the ketal group is cleaved off according to the methods of protective group chemistry that are known to one skilled in the art.

The production of diastereomeric 1,3 diol-ketals of general formulas XIVa and XIVb is carried out from the racemic diol of general formula II by reaction with chiral ketones according to processes that are known in the literature. Lit.: T. Harada et al., J. Org. Chem. 1992, 57, 1412-1421.

Of course, the corresponding enantiomer compounds of general formula Ib

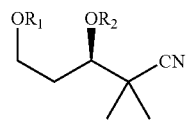

(Ib)

can also be produced with use of mirror-image catalysts or other enzyme systems.

There is also the possibility of obtaining the corresponding enantiomers in intermediate stages of general formula IIIb

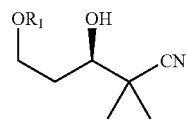

(IIIb)

by inversion of the hydroxyl group according to Mitsunobu (Lit.: Synthesis 1981, 1-28).

Of protective groups R1 and R2 that are used in the synthesis, the benzyl group and the TBDMS group are preferred. In the case that R1, R2 stands for a ketal protective group, especially —(C(CH3)2)— is preferred.

Of the different production variants here, the following partial sequences are especially preferred for the creation of achiral precursors:

1. Production of the compound of general formula VII from the intermediate stages of general formulas V and VIII
   R1=benzyl, Nu=Cl

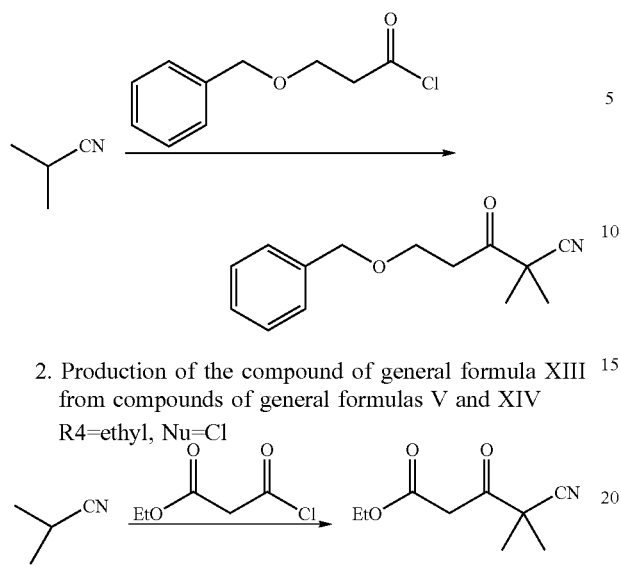

2. Production of the compound of general formula XIII from compounds of general formulas V and XIV
R4=ethyl, Nu=Cl 3. Production of the compounds of general formula VII by aldol condensation and subsequent oxidation
R1=benzyl, Nu=Cl 4. Production of the compounds of general formula IX (with Y=dimethylamino)

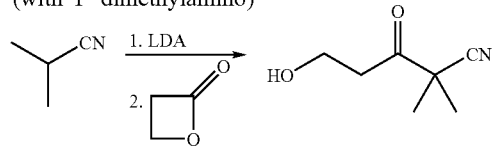

For the production of chiral precursors, especially the partial steps that are indicated below are preferred:

1. Chiral aldol condensation with a chiral catalyst

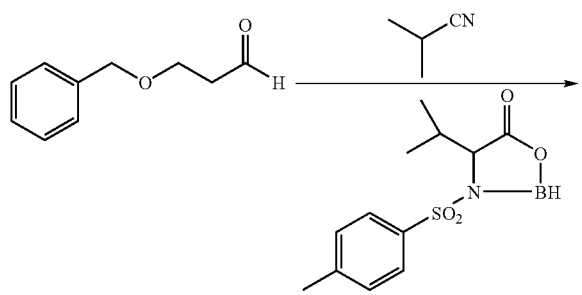

-continued

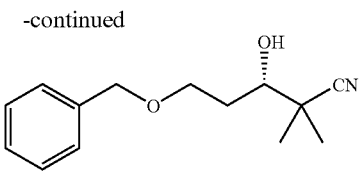

2. Enantioselective saponification of an acetate with the aid of an enzyme

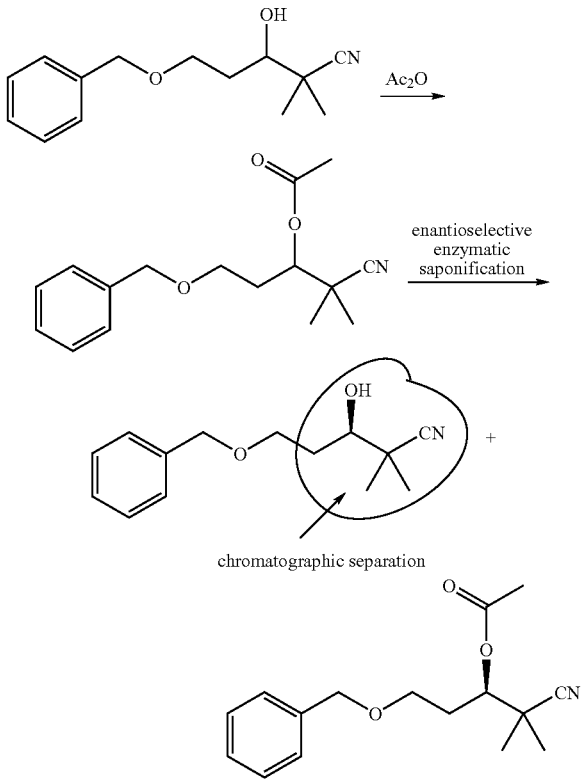

3. Chiral reduction of a β-keto nitrile (Noyori type)

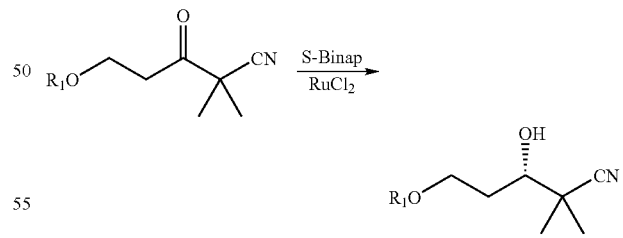

4. Chiral reduction of the β-keto ester with subsequent reduction

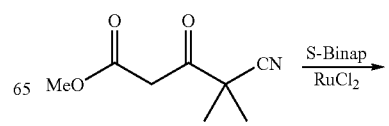

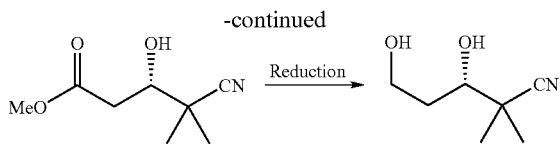

The production of the compounds according to the invention is carried out preferably in the sequences that are described below:

1. Production of acetone ketals

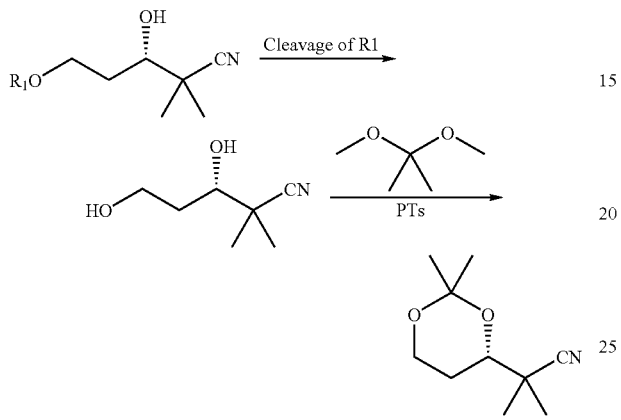

R1 = benzyl => hydrogenation
R1 = THP => acidic cleavage
R1 = TBDMS => TBAF

2. Production of the Di-TBDMS-protected compound

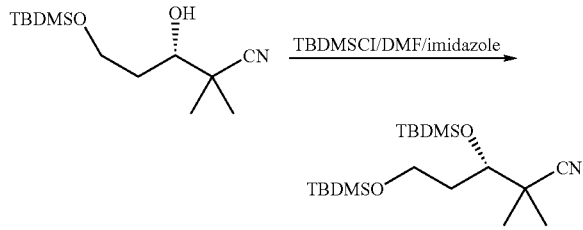

The production of the compounds and process according to the invention is to be explained in more detail in the embodiments below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

EXAMPLE 1a

5-Benzyloxy-2,2-dimethyl-3(R,S)-hydroxy-pentane-nitrile 5.47 g (79.17 mmol) of isobutyric acid nitrile is added in drops at −65° C. to an LDA solution (produced from 33.64 g (79.17 mmol) of n-butyllithium 15% in hexane, (1.6 M) and 80.1 g (79.17 mmol) of diisopropylamine), and it is stirred for 20 minutes at −65° C. Then, a solution that consists of 10 g (60.9 mmol) of 3-benzyloxy-1-propanaldehyde in 20 ml of THF is added in drops (over 60 minutes). The temperature is kept at −65° C.! Then, it is stirred for one more hour. It is now heated to −20° C., a solution that consists of 20% sulfuric acid is added in drops, and the temperature is allowed to reach +10° C. Then, 50 ml of MTB-ether is added, and then the organic phase is separated. The organic phase is washed with water and then with saturated sodium bicarbonate. Finally, it is washed once more with water and then evaporated to the dry state in a vacuum.

Yield: 13.1 g (92% of theory) of a colorless oil.

| | Elementary analysis: | | |
|---|---|---|---|
| | C | H | N |
| Cld. | 72.07 | 8.21 | 6.00 |
| Fnd. | 72.34 | 8.43 | 5.85 |

EXAMPLE 1b

5-Benzyloxy-2,2-dimethyl-3(R,S)-acetoxy-pentane-nitrile 14.56 g (42.64 mmol) of acetic acid anhydride is added at 0° C. to a solution that consists of 25.6 g (109.7 mmol) of 5-benzyloxy-2,2-dimethyl-3-hydroxy-pentane-nitrile of the title compound of Example 1a, 14.43 g (142.64 mmol) of triethylamine and 200 mg of 4-dimethylaminopyridine (DMAP), dissolved in 128 ml of MTB-ether, and it is stirred for 5 hours at room temperature. The reaction mixture is poured onto 2 l of ice water and extracted twice with 300 ml each of MTB-ether. The combined MTB-phases are washed once with 300 ml of 5% hydrochloric acid and then with water. It is evaporated to the dry state in a vacuum.

Yield: 28.82 g (95% of theory) of a colorless oil.

| | Elementary analysis: | | |
|---|---|---|---|
| | C | H | N |
| Cld. | 69.79 | 7.69 | 5.09 |
| Fnd. | 69.51 | 8.01 | 4.83 |

EXAMPLE 1c

5-Benzyloxy-2,2-dimethyl-3(S)-hydroxy-pentane-nitrile 10 g (36.31 mmol) of 5-benzyloxy-2,2-dimethyl-3(R,S)-acetoxy-pentane-nitrile of the title compound of Example 1b is added to a buffer solution, produced from 0.88 g of potassium dihydrogen phosphate and 1.82 g of disodium hydrogen phosphate in 250 ml of water. Then, 5 g of the enzyme lipase AYS "Amano" (related to Amano) is added, and it is stirred for 24 hours at 40° C. The pH is brought to 7 by adding 2.062 g of disodium hydrogen phosphate, and then stirring is continued with HPLC monitoring at intervals of 12 hours with HPLC monitoring until the peak of the R-acetate is less than 1% of the surface area. Working-up: It is extracted twice with 200 ml of ethyl acetate. The organic phases are combined and evaporated to the dry state in a vacuum. The purification is carried out by chromatography on silica gel (hexane/ethyl acetate gradient). With the first fraction, 4.2 g (45% of theory) of 5-benzyloxy-2,2-dimethyl-3(R)-hydroxy-pentane-nitrile is obtained, and with the second fraction, 4.8 g (48% of theory) of 5-benzyloxy-2,2-dimethyl-3(S)-acetoxy-pentane-nitrile is obtained.

4.8 g (17.5 mmol) of 5-benzyloxy-2,2-dimethyl-3(S)-acetoxy-pentane-nitrile from the second fraction is dissolved in 50 ml of methanol and mixed with 1.4 g (35 mmol) of NaOH. It is stirred for 3 hours at 25° C., added to 200 ml of water, extracted with 2×200 ml of MTB ether, dried on sodium sulfate and concentrated by evaporation.

Yield: 4 g (47% of theory) of 5-benzyloxy-2,2-dimethyl-3(S)-hydroxy-pentane-nitrile as a colorless oil.

Elementary analysis:

|  | C | H | N |
|---|---|---|---|
| Cld. | 72.07 | 8.21 | 6.00 |
| Fnd. | 71.85 | 8.41 | 5.87 |

EXAMPLE 1d

5-Hydroxy-2,2-dimethyl-3(S)-hydroxy-pentane-nitrile 16 g of Pearlman's catalyst ($Pd(OH)_2$ on carbon, 20%) is added to 11.13 g (47.70 mmol) of 5-benzyloxy-2,2-dimethyl-3 (S)-hydroxy-pentane-nitrile of the title compound of Example 1c, dissolved in 110 ml of tetrahydrofuran. It is now hydrogenated for 7.5 hours at 10 bar and at room temperature. Catalyst is filtered out, and the filtrate is evaporated to the dry state in a vacuum.

Yield: 6.73 g (98% of theory) of a colorless, viscous oil.

Elementary analysis:

|  | C | H | N |
|---|---|---|---|
| Cld. | 58.72 | 9.15 | 9.78 |
| Fnd. | 58.64 | 9.23 | 9.69 |

EXAMPLE 1e

3(S)-(3,5) Acetone dimethylketal-2,2-dimethyl-pentane-nitrile 6.73 g (47 mmol) of 5-hydroxy-2,2-dimethyl-3(S)-hydroxy-pentane-nitrile of the title compound of Example 1d is dissolved in 27 ml of acetone dimethylketal, and 546 mg of camphor-10-sulfonic acid is added. It is heated for 15 hours to 50° C. It is evaporated to the dry state in a vacuum. The residue is taken up in 200 ml of methylene chloride and washed with saturated sodium bicarbonate solution and then with saturated sodium chloride solution. The organic phase is dried on sodium sulfate and evaporated to the dry state in a vacuum. The oil that is obtained crystallizes while standing.

Yield: 5.55 g, (77% of theory) of colorless crystalline solid.

Elementary analysis:

|  | C | H | N |
|---|---|---|---|
| Cld. | 65.54 | 9.35 | 7.64 |
| Fnd. | 65.38 | 9.29 | 7.58 |

EXAMPLE 2

3(S)-3,5-Di-tert-butyldimethylsilyloxy-2,2-dimethyl-pentane-nitrile 7.13 g (104.75 mmol) of imidazole and 7.9 g (52.37 mmol) of tert-butyldimethylsilyl chloride are added to a solution that consists of 3 g (20.95 mmol) of 5-hydroxy-2,2-dimethyl-3(S)-hydroxy-pentane-nitrile of the title compound of Example 1d, in 20 ml of dimethylformamide, and it is stirred for 16 hours at room temperature. The solution is poured onto 200 ml of water and extracted twice with 50 ml of cyclohexane each. The organic phases are combined and evaporated to the dry state in a vacuum. The residue is purified by flash chromatography on silica gel (hexane/MTB ether).

Yield: 7.39 g, (95% of theory) of a colorless, viscous oil.

Elementary analysis:

|  | C | H | N |
|---|---|---|---|
| Cld. | 61.39 | 11.12 | 3.77 |
| Fnd. | 62.00 | 11.30 | 3.80 |

EXAMPLE 3

3(S)-3,5-Cyclohexanone-dimethylketal-2,2-dimethyl-pentane-nitrile 10 mg of p-toluenesulfonic acid is added to a solution that consists of 3 g (20.95 mmol) of 5-hydroxy-2,2-dimethyl-3(S)-hydroxy-pentane-nitrile of the title compound of Example 1f in 30.21 g (0.2095 mol) of cyclohexanone-dimethylketal, and it is stirred for 6 hours at 100° C. The solution is poured onto 200 ml of water and extracted twice with 50 ml of ethyl acetate each. The organic phases are combined and evaporated to the dry state in a vacuum. The residue is purified by flash chromatography on silica gel (hexane/MTB-ether).

Yield: 4.21 g (90% of theory) of a colorless, viscous oil.

Elementary analysis:

|  | C | H | N |
|---|---|---|---|
| Cld. | 69.92 | 9.48 | 6.27 |
| Fnd. | 69.81 | 9.62 | 6.15 |

EXAMPLE 4

3(S)-3,5-Benzaldehyde-dimethylacetal-2,2-dimethyl-pentane-nitrile 31.9 g (0.2095 mol) of benzaldehyde-dimethylacetal and 50 mg of p-toluenesulfonic acid are added to a solution that consists of 3 g (20.95 mmol) of 5-hydroxy-2,2-dimethyl-3 (S)-hydroxy-pentane-nitrile of the title compound of Example 1f, in 20 ml of dimethylformamide, and it is stirred for 16 hours at 100° C. The solution is poured onto 200 ml of water and extracted twice with 50 ml of ethyl acetate each. The organic phases are combined and evaporated to the dry state in a vacuum. The residue is purified by flash chromatography on silica gel (hexane/MTB-ether).

Yield: 4.26 g (88% of theory) of a colorless, viscous oil.

| Elementary analysis: | | | |
|---|---|---|---|
| | C | H | N |
| Cld. | 69.92 | 9.48 | 6.27 |
| Fnd. | 69.81 | 9.62 | 6.15 |

EXAMPLE 5

3(S)-3,5-Dichlorodiphenylsilane-2,2-dimethyl-pentane-nitrile 3.14 g (46.09 mmol) of imidazole and 5.83 g (23.05 mmol) of dichlorodiphenylsilane are added to a solution that consists of 3 g (20.95 mmol) of 5-hydroxy-2,2-dimethyl-3(S)-hydroxy-pentane-nitrile of the title compound of Example 1f, in 20 ml of dimethylformamide, and it is stirred for 16 hours at room temperature. The solution is poured onto 200 ml of water and extracted twice with 50 ml of methylene chloride each. The organic phases are combined and evaporated to the dry state in a vacuum. The residue is purified by flash chromatography on silica gel (hexane/MTB-ether).

Yield: 5.76 g (85% of theory) of a colorless, viscous oil.

| Elementary analysis: | | | |
|---|---|---|---|
| | C | H | N |
| Cld. | 70.55 | 6.54 | 4.33 |
| Fnd. | 70.41 | 6.71 | 4.25 |

EXAMPLE 6a 5-tert-Butyldimethylsilyl-2,2-dimethyl-3(R,S)-hydroxy-pentane-nitrile 4.62 g (66.99 mmol) of isobutyric acid nitrile is added in drops at −65° C. to an LDA solution (produced from 28.6 g (66.99 mmol) of n-butyllithium 15% (1.6 M) and 6.82 g, 66.99 mmol, of diisopropylamine), and it is stirred for 20 minutes at −65° C. Then, a solution that consists of 11.47 g (60.9 mmol) of 5-tert-butyldimethylsilyl-1-propanaldehyde in 20 ml of THF is added in drops (over 60 minutes). The temperature is held at −65° C.! Then, it is stirred for one more hour. It is now heated to −20° C., and a solution of 130 ml of 1N hydrochloric acid is added in drops, and the temperature is allowed to come to +10° C. Then, 50 ml of MTB-ether is added, and then the organic phase is separated. The organic phase is washed with water and then saturated sodium bicarbonate solution. Finally, it is washed once more with water and then evaporated to the dry state in a vacuum.

Yield: 13.65 g (87% of theory).

| Elementary analysis: | | | |
|---|---|---|---|
| | C | H | N |
| Cld. | 60.65 | 10.57 | 5.44 |
| Fnd. | 60.48 | 10.65 | 5.37 |

EXAMPLE 6b

5-Hydroxy-2,2-dimethyl-3(R,S)-hydroxy-pentane-nitrile 12.18 g (46.61 mmol) of tetrabutylammonium fluoride hydrate is added to a solution that consists of 3 g (11.65 mmol) of 5-tert-butyldimethylsilyl-2,2-dimethyl-3(R,S)-hydroxy-pentane-nitrile of the title compound of Example 6a, dissolved in 40 ml of tetrahydrofuran, and it is stirred for 16 hours at room temperature. Then, it is evaporated to the dry state in a vacuum. The residue is purified by RP-18 chromatography (mobile solvent: acetonitrile/water gradient).

Yield: 1.41 g (85% of theory) of a colorless, viscous oil.

| Elementary analysis: | | | |
|---|---|---|---|
| | C | H | N |
| Cld. | 58.72 | 9.15 | 9.78 |
| Fnd. | 58.51 | 9.23 | 9.64 |

EXAMPLE 6c (−)-Camphor Ketal

3(S)-(3,5) Camphordimethylketal-2,2-dimethyl-pentane-nitrile 6.73 g (47 mmol of 5-hydroxy-2,2-dimethyl-3(R,S)-hydroxy-pentane-nitrile of the title compound of Example 6b, dissolved in 27 ml of methylene chloride, is added with 93 g of (1S)-(−)-camphor ketal (produced from (1S)-(−)-camphor, methanol and p-toluenesulfonic acid), and 546 mg of camphor-10-sulfonic acid. It is refluxed for 15 hours. The batch is diluted in 200 ml of methylene chloride and washed with saturated sodium bicarbonate solution, then with saturated sodium chloride solution. The organic phase is dried on sodium sulfate and evaporated to the dry state in a vacuum. The residue is chromatographed on a chiral phase (mobile solvent: acetonitrile/water gradient). The oil that is obtained crystallizes while standing.

Yield: 10 g, (77% of theory) of a colorless, crystalline solid.

| Elementary analysis: | | | |
|---|---|---|---|
| | C | H | N |
| Cld. | 73.61 | 9.81 | 5.05 |
| Fnd. | 73.40 | 9.79 | 5.00 |

EXAMPLE 6d

5-Hydroxy-2,2-dimethyl-3(S)-hydroxy-pentane-nitrile

Cleavage of the Camphor Ketal 13 g (47 mmol) of 3(S)-(3,5) camphordimethylketal-2,2-dimethyl-pentane-nitrile of the compound of Example 6c is dissolved in 40 ml of tetrahydrofuran, 12.18 g (46.61 mmol) of tetrabutylammonium fluoride hydrate is added, and it is stirred for 16 hours at room temperature, then it is evaporated to the dry state in a vacuum. The residue is purified by RP-18 chromatography (mobile solvent: acetonitrile/water gradient).

Yield: 5.72 g (85% of theory) of a colorless, viscous oil.

Elementary analysis:

|  | C | H | N |
|---|---|---|---|
| Cld. | 58.72 | 9.15 | 9.78 |
| Fnd. | 58.60 | 9.00 | 9.60 |

EXAMPLE 7

5-Benzyloxy-2,2-dimethyl-(S)-hydroxy-pentane-nitrile and

5-Benzyloxy-2,2-dimethyl-3(R)-hydroxy-pentane-nitrile

The title compound of Example 1a, 5-benzyloxy-2,2-dimethyl-3(R,S)-hydroxy-pentane-nitrile, is chromatographed on a chiral phase (10 g on Chiralpak AD 20μ/eluant: hexane/ethanol 98:2, wavelength: 208 nm).

The following are obtained:

R-Isomer, yield: 3.8 g (38% of theory) of a colorless, viscous oil.

Elementary analysis:

|  | C | H | N |
|---|---|---|---|
| Cld. | 58.72 | 9.15 | 9.78 |
| Fnd. | 58.59 | 9.31 | 9.71 |

S-Isomer, yield: 4.1 g (41% of theory) of a colorless, viscous oil.

Elementary analysis:

|  | C | H | N |
|---|---|---|---|
| Cld. | 58.72 | 9.15 | 9.78 |
| Fnd. | 58.61 | 9.27 | 9.69 |

EXAMPLE 8a 5-tert-Butyldimethylsilyl-2,2-dimethyl-3(R,S)acetoxy-pentane-nitrile 14.43 g (142.64 mmol) of triethylamine and 200 mg of 4-dimethylaminopyridine (DMAP), dissolved in 128 ml of MTB-ether, and, at 0° C., 14.56 g (142.64 mmol) of acetic acid anhydride are added to 28.24 g (109.7 mmol) of 5-tert-butyldimethylsilyl-2,2-dimethyl-3(R,S)-hydroxy-pentane-nitrile, the title compound of Example 6a, and it is stirred for 5 hours at room temperature. It is poured onto 2 l of ice water and extracted twice with 300 ml each of MTB-ether. The combined MTB-phases are washed once with 300 ml of 5% hydrochloric acid and then with water. It is evaporated to the dry state in a vacuum. The residue is purified by flash chromatography on silica gel (hexane/MTB-ether).

Yield: 31.21 g (95% of theory) of a colorless oil.

Elementary analysis:

|  | C | H | N |
|---|---|---|---|
| Cld. | 60.16 | 9.76 | 4.68 |
| Fnd. | 60.02 | 9.85 | 4.59 |

EXAMPLE 8b 5-tert-Butyldimethylsilyl-2,2-dimethyl-3(S)hydroxy-pentane-nitrile 10 g (33.39 mmol) of 5-tert-butyldimethylsilyl-2,2-dimethyl-3(R,S)-acetoxy-pentane-nitrile of the title compound of Example 8a is added to a buffer solution, produced from 0.88 g of potassium dihydrogen phosphate and 1.82 g of disodium hydrogen phosphate in 250 ml of water. Then, 5 g of the enzyme lipase AYS "Amano" (related to Amano) is added, and it is stirred for 42.5 hours at room temperature. The pH is brought to 7 by adding 2.062 g of sodium hydrogen phosphate, and then stirring is continued for 44.5 hours. Working-up: It is extracted 3 times with 200 ml of ethyl acetate. The organic phases are combined and evaporated to the dry state in a vacuum. The purification is carried out by chromatography on silica gel (hexane/ethyl acetate gradient).

3.8 g (45%) of 5-tert-butyldimethylsilyl-2,2-dimethyl-3 (R)-hydroxy-pentane-nitrile and 4.8 g (48%) of 5-tert-butyldimethylsilyl-2,2-dimethyl-3(S)-acetoxy-pentane-nitrile are obtained.

4.8 g (16 mmol) of 5-tert-butyldimethylsilyl-2,2-dimethyl-3(S)-acetoxy-pentane-nitrile is dissolved in 50 ml of ethanol and mixed with 1.28 g of NaOH (32 mmol). It is stirred for 3 hours at 25° C., added to 200 ml of water, extracted with 2×200 ml of MTB ether, dried on sodium sulfate and concentrated by evaporation.

Yield: 3.43 g (40% of theory)

Elementary analysis:

|  | C | H | N |
|---|---|---|---|
| Cld. | 60.65 | 10.57 | 5.44 |
| Fnd. | 60.54 | 10.64 | 5.37 |

EXAMPLE 8c

3(S)-3,5-Di-tert-butyldimethylsilyloxy-2,2-dimethyl-pentane-nitrile 2.37 g (34.95 mmol) of imidazole and 2.63 g (17.47 mmol) of tert-butyldimethylsilyl chloride are added to a solution that consists of 3 g (11.65 mmol) of 5-tert-butyldimethylsilyl-2,2-dimethyl-3(S)-hydroxy-pentane-nitrile of the title compound of Example 8b, dissolved in 10 ml of dimethylformamide, and it is stirred for 16 hours at room temperature. The solution is poured onto 100 ml of water and extracted twice with 50 ml of MTB-ether each. The organic phases are combined and evaporated to the dry state in a vacuum. The residue is purified by flash chromatography on silica gel (hexane/MTB-ether).

Yield: 4.11 g (95% of theory) of a colorless, viscous oil.

Elementary analysis:

|      | C     | H     | N    |
|------|-------|-------|------|
| Cld. | 61.39 | 11.12 | 3.77 |
| Fnd. | 61.31 | 11.25 | 3.64 |

EXAMPLE 9

5-Hydroxy-2,2-dimethyl-3(S)-hydroxy-pentane-nitrile 12.18 g (46.61 mmol) of tetrabutylammonium fluoride hydrate is added to a solution that consists of 3 g (11.65 mmol) of 5-tert-butyldimethylsilyl-2,2-dimethyl-3(S)hydroxy-pentane-nitrile of the title compound of Example 8b, dissolved in 40 ml of tetrahydrofuran, and it is stirred for 16 hours at room temperature. Then, it is evaporated to the dry state in a vacuum. The residue is purified by RP-18 chromatography (mobile solvent: acetonitrile/water gradient).

Yield: 1.41 g (85% of theory) of a colorless, viscous oil.

Elementary analysis:

|      | C     | H    | N    |
|------|-------|------|------|
| Cld. | 58.72 | 9.15 | 9.78 |
| Fnd. | 58.61 | 9.23 | 9.69 |

EXAMPLE 10a

5-Benzyloxy-2,2-dimethyl-3-keto-pentane-nitrile 5.47 g (79.17 mmol) of isobutyric acid nitrile is added in drops at −65° C. to an LDA solution (produced from 33.64 g (79.17 mmol) of n-butyllithium (15%, 1.6M) and 80.1 g (79.17 mmol) of diisopropylamine), and it is stirred for 20 minutes at −65° C. Then, a solution that consists of 14.29 g (71.97 mmol) of 3-benzyloxy-1-propionic acid chloride in 20 ml of THF is added in drops (60 minutes). The temperature is held at −65° C.! Then, stirring is continued for one hour. It is heated to −20° C., and a solution that consists of 20% sulfuric acid is added in drops, and the temperature is allowed to reach +10° C. Then, 50 ml of MTB-ether is added, and then the organic phase is separated. The organic phase is washed with water and then with saturated sodium bicarbonate solution. Finally, it is washed once more with water and then evaporated to the dry state in a vacuum. The residue is purified by flash chromatography on silica gel (hexane/MTB-ether).

Yield: 14.15 g (85% of theory) of a colorless, viscous oil.

Elementary analysis:

|      | C     | H    | N    | O     |
|------|-------|------|------|-------|
| Cld. | 72.70 | 7.41 | 6.06 | 13.83 |
| Fnd. | 72.54 | 7.58 | 5.87 |       |

EXAMPLE 10b

5-Hydroxy-2,2-dimethyl-3-keto-pentane-nitrile 3 g of Pearlman's catalyst (Pd(OH)$_2$ on carbon, 20%) is added to 10 g (43.23 mmol) of 5-benzyloxy-2,2-dimethyl-3-keto-pentane-nitrile of the title compound of Example 10a, dissolved in 100 ml of methanol. It is now hydrogenated for 7.5 hours at 10 bar and at room temperature. Catalyst is filtered out, and the filtrate is evaporated to the dry state in a vacuum.

Yield: 5.98 g (98% of theory) of a colorless, viscous oil.

Elementary analysis:

|      | C     | H    | N    |
|------|-------|------|------|
| Cld. | 59.56 | 7.85 | 9.92 |
| Fnd. | 59.47 | 7.94 | 9.85 |

EXAMPLE 10c

3(S),5-Dihydroxy-2,2-dimethyl-pentane-nitrile 5 g (35.41 mmol) of 5-hydroxy-2,2-dimethyl-3-keto-pentane-nitrile of the title compound of Example 10b is hydrogenated with a catalyst (produced from 233 mg of RuCl$_2$ (Ph)$_2$ and 626 mg of R-BINAP according to R. Selke, Angew. Chem. [Applied Chem.] 1998, 110, pp. 1927-1930) (at 40° C. and 100 bar). Catalyst is filtered out, and the filtrate is evaporated to the dry state in a vacuum.

Yield: 4.96 g (98% of theory) of a colorless, viscous oil.

Elementary analysis:

|      | C     | H    | N    |
|------|-------|------|------|
| Cld. | 58.72 | 9.15 | 9.78 |
| Fnd. | 58.65 | 9.26 | 9.71 |

EXAMPLE 11

S-3-(2,2-Dimethyl-[1,3]dioxan-4-yl)-3-methyl-butan-2-one 35.6 ml of methyllithium-lithium bromide complex (1.5 M in diethyl ether) is added in drops at −20° C. to 3.26 g (17.79 mmol) of the title compound of Example 1e, 3(S)-(3,5)-acetone dimethylketal-2,2-dimethyl-pentane-nitrile, dissolved in 5 ml of diethyl ether. Then, it is stirred for 30 minutes at −20° C. and then heated to room temperature. It is stirred overnight at room temperature. 10 ml of saturated ammonium chloride solution is added, and it is stirred for 6 hours at room temperature. The organic phase is separated and washed twice with water. The organic phase is evaporated to the dry state in a vacuum. The purification is carried out by chromatography on silica gel (hexane/ethyl acetate gradient).

Yield: 2.77 g (78% of theory) of an oil.

Elementary analysis:

|  | C | H |
|---|---|---|
| Cld. | 65.97 | 10.07 |
| Fnd. | 65.84 | 10.19 |

EXAMPLE 12

S-1,3-Bis-(tert-butyl-dimethyl-silanyloxy)-4,4-dimethyl-pentan-5-one 40.35 ml of lithium ethylate (1 M solution in THF) is added in drops at −20° C. to 5 g (13.45 mmol) of the title compound of Example 2, 3(S)-3,5-di-tert-butyldimethylsilyloxy-2,2-dimethyl-pentane-nitrile, dissolved in 5 ml of diethyl ether. Then, it is stirred for 30 minutes at −20° C., and then heated to room temperature. It is stirred overnight at room temperature. 10 ml of saturated ammonium chloride solution is added, and it is stirred for 6 hours at room temperature. The organic phase is separated and washed twice with water. The organic phase is evaporated to the dry state in a vacuum. The purification is carried out by chromatography on silica gel (hexane/ethyl acetate gradient).

Yield: 4.06 g (75% of theory) of an oil

Elementary analysis:

|  | C | H |
|---|---|---|
| Cld. | 62.63 | 11.51 |
| Fnd. | 62.51 | 11.64 |

EXAMPLE 13

S-2-(2,2-Dimethyl-[1,3]dioxan-4-yl)-2-methyl-heptan-3-one 34 ml of n-butyllithium, 15% (1.6 M in hexane) is added in drops at −65° C. [to] 3.26 g (17.79 mmol) of the title compound of Example 1e, 3(S)-(3,5)-acetone dimethylketal-2,2-dimethyl-pentane-nitrile, dissolved in 5 ml of THF. Then, it is stirred for five hours at −65° C., and then it is heated to room temperature. It is stirred overnight at room temperature. 10 ml of saturated ammonium chloride solution is added, and it is stirred for 6 hours at room temperature. The organic phase is separated and washed twice with water. The organic phase is evaporated to the dry state in a vacuum. The purification is carried out by chromatography on silica gel (hexane/ethyl acetate gradient).

Yield: 4.13 g (96% of theory) of an oil

Elementary analysis:

|  | C | H |
|---|---|---|
| Cld. | 69.38 | 10.81 |
| Fnd. | 69.27 | 10.96 |

EXAMPLE 14

(4S)-4-(2-Methyl-3-oxo-hept-6-en-2-yl)-2,2-dimethyl-(1,3)dioxane 50 ml of 3-butenyllithium solution (produced from 4-bromo-1-butenes and lithium wire or tert-butyllithium, according to J. Org. Chem. Vol. 56 No. 21, pp. 6094-6103 (1991) or J. Chem. Soc. Perkin Trans. 1 pp. 2937 (1988)) is added in drops at −90° C. to 3.26 g (17.79 mmol) of the title compound of Example 1e, 3(S)-(3,5)-acetone dimethylketal-2,2-dimethyl-pentane-nitrile, dissolved in 5 ml of diethyl ether. Then, it is stirred for 17 hours at −90° C. and then heated to room temperature. It is stirred overnight at room temperature for 17 hours. 10 ml of saturated ammonium chloride solution is added, and it is stirred for 6 hours at room temperature. The organic phase is separated and washed twice with water. The organic phase is evaporated to the dry state in a vacuum. The purification is carried out by chromatography on silica gel (hexane/ethyl acetate gradient).

Yield: 2.74 g (70% of theory) of a colorless oil.

Elementary analysis:

|  | C | H |
|---|---|---|
| Cld. | 69.96 | 10.06 |
| Fnd. | 69.90 | 10.00 |

Abbreviations of the Ether Protective Groups that are Used:

| TES = | Triethylsilyl |
|---|---|
| TMS = | Trimethylsilyl |
| TIP = | Triisopropyl |
| TBDPS = | tert-Butyl-dimethylsilyl |
| MEM = | Methylethoxymethyl |
| MOM = | Methyloxymethyl |
| THP = | Tetrahydropyranyl-(ether) |

The entire disclosures of all applications, patents and publications, cited herein and of corresponding German Application No. 101 38 347.9, filed Aug. 3, 2001, and U.S. Provisional Application Ser. No. 60/313,016, filed Aug. 20, 2001 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula

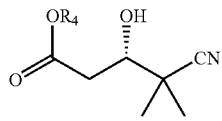

in which

R$_4$ stands for a C1-C6 alkyl, phenyl or benzyl group.

2. A method for making a compound according to claim 1, which comprises performing a chiral reduction on a compound of the following formula XIII:

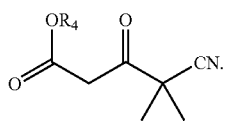

(XIII)

3. A compound of the following formula XIII:

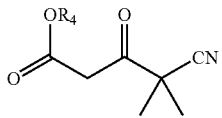

(XIII)

in which

R$_4$ stands for a C1-C6 alkyl, phenyl or benzyl group.

4. A compound of formula

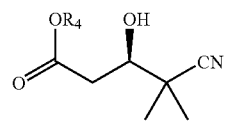

(XII')

in which

R$_4$ stands for a C1-C6 alkyl, phenyl or benzyl group.

5. The compound of claim 1, wherein R$_4$ is methyl, ethyl or tert-butyl.

6. The compound of claim 3, wherein R$_4$ is methyl, ethyl or tert-butyl.

7. The compound of claim 4, wherein R$_4$ is methyl, ethyl or tert-butyl.

* * * * *